United States Patent [19]

Saito et al.

[11] Patent Number: 5,384,409
[45] Date of Patent: Jan. 24, 1995

[54] PROCESS FOR PRODUCING 5-AMINO-3-METHYLPYRAZOLE

[75] Inventors: Kenji Saito, Hirakata; Masahito Sekiguchi, Ibaraki; Shinzaburo Masaki, Toyonaka; Hiroshi Yoshihara, Oita; Kazuhiko Takahashi, Ibaraki; Kazuya Minamisaka, Takaishi; Takashi Kawai, Kobe, all of Japan

[73] Assignee: Sumitomo Chemical Company, Limited, Osaka, Japan

[21] Appl. No.: 66,033

[22] PCT Filed: Sep. 28, 1992

[86] PCT No.: PCT/JP92/01233
§ 371 Date: May 26, 1993
§ 102(e) Date: May 26, 1993

[87] PCT Pub. No.: WO93/06088
PCT Pub. Date: Apr. 1, 1993

[30] Foreign Application Priority Data

Sep. 27, 1991 [JP] Japan ................... 3-249040
Sep. 27, 1991 [JP] Japan ................... 3-249051
Jul. 29, 1992 [JP] Japan ................... 4-202338

[51] Int. Cl.6 ........................................... C07D 231/38
[52] U.S. Cl. ................................................. 548/371.4
[58] Field of Search ..................................... 548/371.4

[56] References Cited

U.S. PATENT DOCUMENTS 2,975,188  3/1961  Gold et al. .
3,920,693  11/1975  Ege .

FOREIGN PATENT DOCUMENTS 0370357  5/1990  European Pat. Off. .
1224884  6/1960  France .
2044654  3/1972  Germany .
3714834  11/1988  Germany .
47-6179  4/1972  Japan .
50-96567  7/1975  Japan .

OTHER PUBLICATIONS

*Chemical Abstracts*, vol. 81, 1974, p. 525, Abstract No. 105429x, Ermitas Alcalde et al., "Reaction of β-aminocrotononitrile and α-formylphenylacetonitrile with hydrazine".
*Chemical Abstracts*, vol. 114, 1991, p. 793, Abstract No. 185496e, Akira Ogawa et al., "Preparation of 5-amino--3-alkyl-4-chloro-1H—".
*Chemical Abstracts*, vol. 50, Abstract No. 4195g, Peter Kurtz, "Nitriles" (1954).
*Chemical Abstracts*, vol. 71, 1969, p. 323, Abstract No. 80741w, Goro Kimura et al., "Chlorovinylacetonitrile".
*Chemical Abstracts*, vol. 111, 1989, p. 663, Abstract No. 115168p, Reinhard Lantzsch, "Preparation of 5-amino-1-aryl-3-methylpyrazoles as insecticide intermediates".
*J. Heterocylic Chem.*, vol. 19, Nov.–Dec. 1982, pp. 1267-1273, Günter Ege et al., "Aminopyrazoles. IV (1). Pyrazol-3- and 5-amines from 2,3-Dihaloalkanenitriles or 3-Chloroacrylonitriles and Hydrazines".
*Chemical Abstracts*, vol. 55, Abstract No. 11307h, Peter Kurtz, "Allenic nitriles" (1961).
*Chemical Abstracts*, vol. 59, Abstract No. 441e, Roger Vessiere et al., "Reactions of 3-bromo-3-butenenitrile and ethyl 3-bromo-3-butenoate. Preparation of 2-butynenitrile" (1963).
*Chemical Abstracts*, vol. 55, Abstract No. 25988c, Heinrich Gold et al., "Substituted 5-aminopyrazoles" (1959).
*Chemical Abstracts*, vol. 54, No. 2, 25 Jan. 1960, Columbus, Ohio, US; Abstract No. 275i, P. Kurtz et al., "Nitrile formation III" & vol. 624, 1959, pp. 1-25, Ann.
*Journal of Heterocyclic Chemistry*, vol. 19, No. 6, 1982, Provo, Utah, US, pp. 1267-1273, G. Ege et al., "Aminopyrazoles. IV.".

Primary Examiner—Robert W. Ramsuer
Attorney, Agent, or Firm—Stevens, Davis, Miller & Mosher

[57] ABSTRACT

A process for producing 5-amino-3-methylpyrazole which comprises reacting hydrazine with a reaction intermediate containing at least one compound selected from the group consisting of 3-chloro-3-butenonitrile and 2,3-butadienenitrile, which intermediate is obtainable from 2,3-dichloropropene and hydrocyanic acid.

A process for producing 5-amino-4-chloro-3-methylpyrazole which comprises chlorinating 5-amino-3-methylpyrazole obtainable by the above-mentioned reaction, in the presence of hydrochloric acid.

8 Claims, No Drawings

PROCESS FOR PRODUCING 5-AMINO-3-METHYLPYRAZOLE

TECHNICAL FIELD

The present invention relates to a process for producing 5-amino-3-methylpyrazole.

BACKGROUND ART

5-Amino-3-methylpyrazole is a compound well known as an intermediate used in the field of fine chemicals (e.g., photographic chemicals, medicines and agricultural chemicals). It has also been known that the compound can be produced, for example, by the following methods.

(1) A method which comprises reacting acetonitrile with metallic sodium, sodium hydride or the like to obtain diacetonitrile, and reacting diacetonitrile with hydrazine (for example, J. Heterocyclic Chem., 11, 423 (1974)).

(2) A method which comprises reacting crotononitrile with chlorine to obtain 2,3-dichlorobutyronitrile, dehydrochlorinating 2,3-dichlorobutyronitrile in the presence of a base (e.g., potassium t-butoxide) to obtain 2-chloro-2-butenonitrile, and reacting 2-chloro-2-butenonitrile with hydrazine (for example, J. Heterocyclic Chem., 19, 1267 (1982)).

(3) A method which comprises reacting sodium cyanide with propargyl chloride to form 2,3-butadienenitrile and reacting 2,3-butadienenitrile with hydrazine (for example, Ann., 624, 1 (1959)).

However, the method (1) has a problem of using such agents having the danger of spontaneous ignition as metallic sodium and sodium hydride. The method (2) has a problem that crotononitrile, a starting material, is expensive. The method (3) has a problem of using explosive propargyl chloride.

DISCLOSURE OF THE INVENTION

The present inventors have made extensive study to find a process for producing 5-amino-3-methylpyrazole without using such agents and starting material that would cause the problems as mentioned above. As the result, they have found a novel process for producing 5-amino-3-methylpyrazole which comprises reacting 2,3-dichloropropene with hydrocyanic acid to obtain a reaction mixture and reacting the reaction mixture with hydrazine. Thus, they accomplished the present invention.

The first aspect of the present invention relates to a process for producing 5-amino-3-methylpyrazole which comprises the steps of:

(a) reacting hydrocyanic acid with 2,3-dichloropropene in the presence of water and a cuprous salt at a pH of from 3 to 8 to obtain a reaction intermediate containing at least one compound selected from the group consisting of 3-chloro-3-butenonitrile and 2,3-butadienenitrile, and (b) reacting hydrazine with the reaction intermediate.

The second aspect of the present invention relates to a process for producing 5-amino-3-methylpyrazole which comprises the steps of:

(a) reacting hydrocyanic acid with 2,3-dichloropropene in the presence of water and a cuprous salt at a pH of from 3 to 8 to obtain a reaction mixture containing 3-chloro-3-butenonitrile, (b) reacting a base with the reaction mixture to obtain 2,3-butadienenitrile, and (c) reacting 2,3-butadienenitrile with hydrazine.

The third aspect of the present invention relates to a process for producing 5-amino-4-chloro-3-methylpyrazole hydrochloride which comprises the steps of:

(a) reacting at least one compound selected from the group consisting of 3-chloro-3-butenonitrile and 2,3-butadienenitrile with hydrazine to obtain 5-amino-3-methylpyrazole, and (b) chlorinating 5-amino-3-methylpyrazole in the presence of hydrochloric acid.

2,3-Dichloropropene used in the first step of the first aspect is known to the art, which aspect relates to a process for producing 5-amino-3-methylpyrazole which comprises the steps of: (a) reacting hydrocyanic acid with 2,3-dichloropropene in the presence of water and a cuprous salt at a pH of 3-8 to obtain a reaction intermediate containing at least one compound selected from the group consisting of 3-chloro-3-butenonitrile and 2,3-butadienenitrile, and (b) reacting hydrazine with the reaction intermediate.

The cuprous salt used in the reaction of 2,3-dichloropropene with hydrocyanic acid may be, for example, cuprous chloride, cuprous cyanide, and the like. The amount used of the cuprous salt is usually within the range of from 0.01 to 1 equivalent, preferably within the range of from 0.01 to 0.05 equivalent, relative to 2,3-dichloropropene.

Hydrocyanic acid is used in an amount of usually 1–2 equivalents relative to 2,3-dichloropropene.

The reaction is conducted in the presence of water. Water is usually used in an amount of at least 10 times by weight, preferably at least 13 times by weight, relative to the cuprous salt.

Although water is most preferably used as the reaction solvent, polar solvents such as ethylene glycol, dimethylformamide and dimethyl sulfoxide, aromatic hydrocarbon solvents represented by toluene, hydrocarbon solvents such as hexane and heptane, and the mixtures thereof, may be added to water. In the case where these solvents are used in combination with water, they are used in an amount of 1–10 times by weight relative to 2,3-dichloropropene.

This reaction is usually conducted by dropwise adding, into a mixture of a solvent and a cuprous salt, 2,3-dichloropropene and hydrocyanic acid each individually or as a mixture.

The reaction temperature is usually between 50° and 120° C.

The reaction of 2,3-dichloropropene with hydrocyanic acid is conducted in the pH range of 3–8, whereby 3-chloro-3-butenonitrile and 2,3-butadienenitrile are formed. The formation ratio of these compounds varies depending on the pH of the reaction liquid. A low pH tends to give 3-chloro-3-butenonitrile in a dominating amount. In contrast, a high pH tends to give 2,3-butadienenitrile in a dominating amount.

In general, 3-chloro-3-butenonitrile can be obtained as the main product by allowing the reaction to proceed with keeping the pH of the reaction liquid within the range between 3 and 6, preferably between 3 and 5. On the other hand, 2,3-butadienenitrile can be obtained as the main product by allowing the reaction to proceed with keeping the pH within the range between 6 and 8.

However, 3-chloro-3-butenonitrile and 2,3-butadienenitrile are both converted to 5-amino-3methylpyrazol through the reaction with hydrazine in the next reaction step, so that either an intermediate containing 3-chloro-3-butenonitrile as the main component or an intermediate containing 2,3-butadienenitrile as the main component may be available for the process of the present invention.

When the pH of the reaction liquid is outside the above-mentioned range, for example when the pH is in the range higher than 8, no 2,3-butadienenitrile, to say nothing of 3-chloro-3-butenonitrile, is obtained due to severe formation of tarry matters.

When the pH of the reaction liquid is lower than 3, the reaction of 2,3-dichloropropene with hydrocyanic acid scarcely proceeds.

This reaction is conducted in the presence of an appropriate amount of a base, or alternatively, with successive addition of a base, in order to keep the pH in the above-mentioned range. Specific examples of usable bases are alkali metal hydroxides such as sodium hydroxide and potassium hydroxide, alkaline earth metal hydroxides such as calcium hydroxide and magnesium hydroxide, alkali metal carbonates such as sodium carbonate and potassium carbonate, alkali metal bicarbonates such as sodium hydrogencarbonate and potassium hydrogen-carbonate, alkaline earth metal carbonates such as calcium carbonate and magnesium carbonate, alkali metal salts of a lower carboxylic acid such as sodium formate and sodium acetate, alkali metal alcoholate such as sodium methylate, sodium ethylate and potassium butoxide, and organic bases such as triethylamine and pyridine. These bases may be used as they are, as an aqueous solution or as an aqueous suspension. Of these, calcium hydroxide and calcium carbonate are particularly preferably used. The amount used of the base is usually between 0.1 and 3 equivalents, preferably between 1 and 2 equivalents, per equivalent of 2,3-dichloropropene.

This reaction can be conducted not only in the presence of a cuprous salt alone but also in the co-presence of a cuprous salt and copper powders. The copper powders used usually have a particle size falling within the approximate range from 30 to 100 meshes. They are used in an amount of up to about 0.5 equivalent relative to the cuprous salt.

Co-presence of sodium iodide in the reaction system encourages the reaction. In this case, the amount used of sodium iodide is usually not more than about 0.5 equivalent, preferably not more than about 0.3 equivalent, relative to 2,3-dichloropropene.

In this reaction, 3-chloro-3-butenonitrile can be obtained in a high yield by conducting the reaction of hydrogen cyanide and 2,3-dichloropropene in an autoclave at 90°–110° C. with hermetical sealing and pressure application for preventing the vaporization loss of hydrogen cyanide in the presence of calcium carbonate, a cuprous salt and water.

After completion of the reaction, the reaction mixture is subjected to conventional methods of after-treatment, namely filtration and separation into layers, to obtain 3-chloro-3-butenonitrile, 2,3-butadienenitrile, or the mixture of the two, depending on the pH of the reaction system. If necessary and desired, the reaction mixture may be subjected to such additional operations as extraction to isolate the products. When an organic solvent is used in the reaction or extraction, the intended products can be collected by distilling off the solvent from the solution of the above-mentioned nitriles obtained after the after-treatment. Further, as occasion demands, the nitriles can be purified by such means as distillation.

Nextly, the step of reacting hydrazine with the reaction product of 2,3-dichloropropene with hydrocyanic acid, which is the second step of the first aspect of the present invention, is described below.

The reaction of 2,3-dichloropropene with hydrocyanic acid gives as the product 3-chloro-3-butenonitrile or 2,3-butadienenitrile, or the mixture of the two as described above. The product can be used as such for the reaction with hydrazine.

The hydrazine used is usually in the form of hydrazine hydrate. It may be anhydrous hydrazine, and also hydrazine formed by reacting a base with a salt of hydrazine and an acid (e.g. hydrochloride, sulfate and acetate). The amount used of hydrazine is usually at least 1 equivalent relative to 2,3-butadienenitrile. For 3-chloro-3-butenonitrile, the amount used of hydrazine is usually within the range of 1.5–3 equivalents due to partial consumption of hydrazine by hydrochloric acid formed in the reaction. However, the amount can be reduced to about 1 equivalent by the addition of a base to the reaction system. After all, the necessary amount of hydrazine is determined by the content of nitriles in the above-mentioned reaction mixture.

Specific examples of the usable base are alkali metal hydroxides such as sodium hydroxide and potassium hydroxide; metal alcoholates such as sodium methylate, sodium ethylate and potassium butylate; alkaline earth metal hydroxides such as calcium hydroxide and magnesium hydroxide; alkali metal carbonates such as sodium carbonate and potassium carbonate; alkali metal bicarbonates such as sodium hydrogencarbonate and potassium hydrogen-carbonate; alkaline earth metal carbonates such as calcium carbonate and magnesium carbonate; and alkali metal salts of lower carboxylic acids such as sodium formate and sodium acetate. These bases may be used as such, or in the form of aqueous solution or aqueous suspension. The amount used of the bases is usually within the range of 0.1–2 equivalents, preferably within the range of 0.5–2 equivalents, relative to 1 equivalent of 3-chloro-3-butenonitrile.

Although the reaction can be conducted without using a solvent, it can be also conducted using, for example, water; alcohols such as methanol, ethanol and butanol; aromatic hydrocarbons such as benzene and toluene; or ethers such as diethyl ether and diisopropyl ether. The amount of these solvents used is not particularly limited.

This reaction is preferably conducted by dropwise adding the reaction product obtained by the preceding reaction into hydrazine hydrate or its aqueous solution. It may, however, be conducted by simultaneously pouring the above-mentioned nitriles and either hydrazine hydrate or their aqueous solution into a reactor. Alternatively, it may be conducted by dropwise adding hydrazine hydrate or its aqueous solution into 3-chloro-3-butenonitrile, 2,3-butadienenitrile, or the mixture of the two.

The reaction temperature is usually within the range of 20°–120° C., preferably within the range of 30°–90° C., more preferably within the range of 50°–80° C.

The solution of 5-amino-3-methylpyrazole thus obtained may be subjected to conventional after-treatment such as extraction, distillation and the like to collect the product, 5-amino-3-methylpyrazole. If necessary, the product may be further purified by such purification means as silica gel column chromatography, recrystallization and the like. Alternatively, the solution of 5-amino-3-methylpyrazole may be used for the next chlorination reaction without being subjected to any after-treatments.

The second aspect of the present invention relates to a process for producing 5-amino-3-methylpyrazole which comprises reacting 2,3-dichloropropene with hydrocyanic acid in the presence of water and a cuprous salt at a pH of from 3 to 8 to obtain a reaction mixture containing 3-chloro-3-butenonitrile, reacting a base with the reaction mixture to obtain 2,3-butadienenitrile, and reacting 2,3-butadienenitrile with hydrazine.

The reaction in the first step of the second aspect of the present invention has been described above. In this reaction, the ratio of 3-chloro-3-butenonitrile to 2,3-butadienitrile formed varies depending on the pH of the reaction system as described above. However, reacting the reaction mixture as it is with a base without subjecting the mixture to any separation procedure converts only 3-chloro-3-butenonitrile in the mixture into 2,3-butadienenitrile through dehydrochlorination. Resultantly, in the next step reaction of the mixture with hydrazine, only 2,3-butadienenitrile reacts with hydrazine. As a result, no hydrogen chloride is by-produced unlike when 3-chloro-3-butenonitrile is present in the reaction system. Therefore, the amount used of hydrazine can advantageously be reduced. Moreover, no addition of a base is required for neutralizing hydrogen chloride during or after the reaction. Thus, the reaction and the after-treatments of the next reaction step can be advantageously simplified. In summary, although this method requires an additional step, it has certain advantages as compared with the method for producing 5-amino-3-methylpyrazole comprising directly reacting 2,3-dichloropropene with hydrocyanic acid to obtain a mixture containing 2,3-butadienenitrile and 3-chloro-3-butenonitrile, and directly reacting the mixture with hydrazine. Accordingly, this method is advantageous when the reaction of the first step is conducted at such a pH that permits the production of 3-chloro-3-butenonitrile in a dominating yield, i.e. at a pH between 3 inclusive and 6 exclusive, more preferably at a pH of from 3 to 5.

Specific examples of the base which can be used in the dehydrochlorination of the second step are alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogencarbonate and potassium hydrogencarbonate; alkaline earth metal carbonates such as calcium carbonate and magnesium carbonate; alkali metal alcoholates such as sodium methylate, sodium ethylate and sodium butoxide; and organic bases such as triethylamine and pyridine. These bases can be used as such or in the form of either aqueous solution or aqueous suspension. Of these, sodium hydroxide, potassium hydroxide and calcium hydroxide are preferably used, and calcium hydroxide is particularly preferred. The amount used of the base is usually within the range of 0.1–3 equivalents, preferably within the range of 0.5–1.5 equivalents, more preferably within the range of 1–1.2 equivalents, relative to 1 equivalent of 3-chloro-3-butenonitrile in the reaction mixture.

The reaction of dehydrochlorination, which is the second step of this method, may be conducted by adding a base into the reaction mixture containing 3-chloro-3-butenonitrile obtained in the first step, or alternatively, by pouring, usually simultaneously, the reaction mixture and the base into a reactor.

The reaction mixture and the base are preferably reacted while regulating the pH of the mixture of the reaction mixture and the base to fall within the range of 6–13.5.

When the pH of the mixture of the reaction mixture and the base is lower than 6, the reaction is decelerated. When the pH of the reaction mixture and the base is higher than 13.5, the yield of the intended 2,3-butadienenitrile is reduced.

The reaction temperature is usually within the range of 0°–100° C., preferably within the range of 10°–50° C.

Although in this method, the reaction mixture containing 3-chloro-3-butenonitrile obtained by the reaction of 2,3-dichloropropene with hydrocyanic acid is used as it is for dehydrochlorination, it is needless to say that 3-chloro-3-butenonitrile isolated from the reaction mixture can be subjected to the dehydrochlorination as a starting material.

After completion of the reaction, the reaction mixture is subjected to filtration and separation into layers, which are conventional after-treatments, to obtain 2,3-butadienenitrile. If necessary, the product thus obtained may be further subjected to such operations as extraction. When an organic solvent is used in the reaction or extraction, the intended product can be collected by distilling off the solvent from the solution of the nitrile. Further, according to necessity, 2,3-butadienenitrile can be purified by such means as distillation.

Thus, 2,3-butadienenitrile is produced. It has already been known to the art, as described above that reacting 2,3-butadienenitrile with hydrazine gives 5-amino-3-methylpyrazole. The conditions for the reaction of 2,3-butadienenitrile with hydrazine are also as described above.

The third aspect of the present invention relates to a process for producing 5-amino-4-chloro-3-methylpyrazole which comprises reacting hydrazine with 3-chloro-3-butenonitrile and/or 2,3-butadienenitrile to obtain 5-amino-3-methylpyrazole, and chlorinating 5-amino-3-methylpyrazole in the presence of hydrochloric acid.

The method for preparing 3-chloro-3-butenonitrile, 2,3-butadienenitrile or the mixture of these nitriles, which are starting materials for the process of the third aspect of the present invention, and the method for obtaining 5-amino-3-methylpyrazole by reacting the nitrile(s) with hydrazine are as same as in the first and second aspects of the present invention.

5-Amino-3-methylpyrazole thus obtained can be used for the next chlorination step as it is contained in the reaction solution from the reaction of the above-mentioned nitriles with hydrazine, skipping over any after-treatments.

In other words, the reaction solution containing 5-amino-3-methylpyrazole itself can be subjected to chlorination in the presence of hydrochloric acid to produce 5-amino-4-chloro-3-methylpyrazole.

In the chlorination, the concentration of hydrochloric acid in the reaction system is not particularly limited. The reaction is usually conducted by adding concentrated hydrochloric acid to the reaction system. It may also be conducted by blowing hydrogen chloride gas into the reaction system.

The amount of pure hydrogen chloride, which is added to the reaction system as hydrochloric acid or hydrogen chloride gas, is usually within the range of 0.5–2 equivalents, preferably within the range of 1.2–1.7 equivalents, relative to 1 equivalent of 5-amino-3-methylpyrazole.

The chlorination can be conducted by using a chlorinating agent such as sulfuryl chloride, chlorine gas, and the like. The chlorinating agent is used in an amount of usually 1–5 equivalents, particularly preferably 1.2–3.0 equivalents, relative to 1 equivalent of 5-amino-3-methylpyrazole.

The chlorination is conducted usually at 0°–50° C., preferably at 10°–30° C.

The reaction solution containing 5-amino-4-chloro-3-methylpyrazole thus obtained is neutralized with an inorganic base. Thereafter, the neutralized reaction solution is treated with an organic solvent to extract 5-amino-4-chloro-3-methylpyrazole. Hydrochloric acid is added to the resulting organic layer, whereby 5-amino-4-chloro-3-methylpyrazole hydrochloride of high purity can be isolated as crystals.

Specific examples of the inorganic base which can be used for neutralization of the reaction solution are alkali metal hydroxides such as sodium hydroxide and potassium hydroxide; alkaline earth metal hydroxides such as calcium hydroxide and magnesium hydroxide; alkali metal carbonates such as sodium carbonate and potassium carbonate; alkali metal bicarbonates such as sodium hydrogencarbonate and potassium hydrogencarbonate; alkaline earth metal carbonates such as calcium carbonate and magnesium carbonate; and alkali metal salts of lower carboxylic acids such as sodium formate and sodium acetate. These bases may be used as such, or in the form of either aqueous solution or aqueous suspension.

Desirably, the reaction solution is neutralized with a base usually to a pH falling within the range of from 5 to 8, preferably to a pH falling within the range of from 6 to 7.5.

When the pH is lower than the range, 5-amino-4-chloro-3-methylpyrazole cannot be thoroughly extracted into the organic layer, so that the yield of 5-amino-4-chloro-3-methylpyrazole is lowered. When the pH is higher than the range, on the contrary, the reaction product is colored owing to the decomposition of 5-amino-4-chloro-3-methylpyrazol, so that the quality of the hydrochloride of the finally produced compound is lowered.

Specific examples of the organic solvent which can be used for extracting 5-amino-4-chloro-3-methylpyrazole are acetic esters such as ethyl acetate and butyl acetate; lower alkyl ethers such as diethyl ether, diisopropyl ether and methyl t-butyl ether; lower alkyl halides such as dichloromethane and dichloroethane; aromatic hydrocarbons such as benzene and toluene; and lower alkyl-substituted furans such as 2-methylfuran and 2,5-dimethylfuran. Of these, particularly preferably used are methyl t-butyl ether and 2-methylfuran.

The concentration of the hydrochloric acid added to the organic solvent solution of 5-amino-4-chloro-3-methylpyrazole is not particularly limited. Usually, concentrated hydrochloric acid is used. Alternatively, hydrogen chloride gas may be blown into the organic solvent solution. The amount of pure hydrogen chloride, which is added as hydrochloric acid or hydrogen chloride gas, is usually within the range of 1–2 equivalents, preferably within the range of 1–1.3 equivalents, relative to 1 equivalent of 5-amino-4-chloro-3-methylpyrazole.

BEST MODE FOR CARRYING OUT THE INVENTION

The present invention will be described in more detail below with reference to Examples; however, the present invention is in no way limited thereto.

Example 1

To a 10-l separable flask were charged 223 g of cuprous chloride, 19 g of copper powder, 976 g of calcium carbonate and 5,850 g of water. Thereto was added by drops 122 g of hydrocyanic acid at 65° C. with stirring over a period of 15 minutes. The resulting reaction mass was kept at 80° C. and thereto was added by drops a liquid mixture of 1,665 g of 2,3-dichloropropene and 486 g of hydrocyanic acid in the course of 4 hours. The liquid mixture-added reaction mass was kept at the same temperature for additional 1 hour. The pH of the thus treated reaction mass was lowered from 5.3 to 3.3. After completion of the reaction, the resulting reaction mass was cooled to 15° C. The cooled reaction mass was filtered and separated into layer to obtain 1,270 g of a light brown oil containing 925.6 g of 3-chloro-3-butenonitrile and 104.3 g of 2,3-butadienenitrile. Distilling the oil gave 789.8 g of a fraction containing 707.7 g (yield: 46%) of 3-chloro-3-butenonitrile and 52.5 g (yield: 5%) of 2,3-butadienenitrile.

Then, 789.8 g of the fraction and 3.6 l of methanol were placed in a 10-l separable flask. 1,494 Grams of 60% hydrazine hydrate was added by drops into the flask with ice-cooling. The inner temperature of the flask was raised up to 73° C. and kept at the same temperature for 3 hours. After completion of the reaction, the reaction solution was stripped of methanol by vacuum distillation and extracted with ethyl acetate. The extract was concentrated by distilling off the solvent to obtain 743.7 g of crude 5-amino-3-methylpyrazole (purity: 88%, yield: 44% based on 2,3-dichloropropene). The crude product was purified by column chromatography to obtain 617.9 g of pure 5-amino-3-methylpyrazole (purity: 99%, yield: 42% based on 2,3-dichloropropene).

Example 2

An oil containing 1127.0 g of 3-chloro-3-butenonitrile and 115.0 g 2,3-butadienenitrile was obtained in the same manner as in Example 1. In a 10-l separable flask were placed 1,270.0 g of the thus obtained oil and 6.0 l of methanol. Thereto was added 2,500.0 g of 60% hydrazine hydrate by drops while ice-cooling the flask. The resulting reaction mass was kept at 70°–75° C. for 3 hours. After completion of the reaction, the reaction mass was stripped of methanol and extracted with ethyl acetate. The extract was concentrated by distilling off ethyl acetate to obtain 1,230.0 g of crude 5-amino-3-methylpyrazole (purity: 86%, yield: 85% based on the total amount charged of 3-chloro-3-butenonitrile and 2,3-butadienenitrile). The crude product was purified by column chromatography to obtain 1,035.1 g of pure 5-amino-3-methylpyrazol (purity: 99%, yield: 82%).

Example 3

A mixture containing 1.9 g (0.03 mole) of 2,3-butadienenitrile and 24.6 g (0.24 mole) of 3-chloro-3-butenonitrile was obtained by repeating the same manner as in Example 1. To 55.1 g of 60% hydrazine hydrate was added 26.7 g of the thus obtained mixture at 70°–80° C. by drops. The hydrazine hydrate-added mixture was kept at 80° C. for 1 hour and then cooled to room temperature. Thus, 77.2 g of a pale yellow solution containing 25.5 g (0.26 mole) of 5-amino-3-methylpyrazole was obtained. The thus obtained reaction mass was extracted with ethyl acetate, and the extract was concentrated by distilling off ethyl acetate to obtain 28.31 g of crude 5-amino-3-methylpyrazole. The crude product was purified by silica gel column chromatography to obtain 24.3 g of 5-amino-3-methylpyrazole (purity: 99%, yield: 92%).

Example 4

Into a 10-l separable flask were charged 186.3 g (1.80 moles) of cuprous chloride, 15.7 g (0.25 mole) of copper powder and 2,400 g of water. To the flask were poured simultaneously, with stirring at 65° C., 97.2 g (3.60 moles) of hydrocyanic acid and 655.4 g (1.70 moles) of 20% calcium hydroxide slurry, to bring the pH of the resulting reaction mass to 6.5. The pH-adjusted reaction mass was then brought up to 80° C. A liquid mixture of 1,344 g (12.00 moles) of 2,3-dichloropropene and 388.8 g (14.40 moles) of hydrocyanic acid was added thereto by drops at 80° C. over a period of 3 hours. During the period, 2,571.3 g (6.94 moles) of 20% calcium hydroxide slurry was added by drops to keep the pH of the reaction mass in the range of 6.0–7.0. The pH-controlled reaction mass was kept at the same temperature for additional 2 hours. During the period, 398.9 g (1.08 moles) of 20% calcium hydroxide slurry was added by drops to keep the pH of the reaction mass in the range of 6.0–7.0.

After completion of the reaction, the reaction mass was cooled to 20° C. The cooled reaction mass was filtered and separated into layers to obtain 531.9 g of a light brown oil of crude 2,3-butadienenitrile containing 60.9 g (o.60 mole) of 3-chloro-3-butenonitrile and 371.1 g (5.70 moles) of 2,3-butadienenitrile.

The light brown oil of crude 2,3-butadienenitrile was distilled to obtain 392.1 g of a fraction containing 352.0 g (5.40 moles, yield: 45.1%) of 2,3-butadienenitrile and 31.0 g (0.31 mole, yield: 2.6%) of 3-chloro-3-butenonitrile.

Then, 39.21 g of the fraction was added by drops over a period of 1 hour to a liquid mixture of 47.68 g (0.57 mole) of 60% hydrazine hydrate and 180 ml of methanol while keeping the liquid mixture at 5° C. or below. Then the resulting reaction mass was kept at the same temperature for 30 minutes, then at 65° C. for 5 hours. Thereafter, 21.88 g (0.06 mole) of 10% aqueous hydrochloric acid solution was added to the resulting reaction mass, which was kept at the temperature for additional 2 hours.

After completion of the reaction, the resulting reaction mass was stripped of methanol, then extracted with ethyl acetate. The extract was concentrated by distilling off ethyl acetate to obtain 53.18 g of crude 5-amino-3-methylpyrazole (purity: 88%, yield: 40.1% based on 2,3-dichloropropene). The crude product was purified by column chromatography to obtain 46.48 g of pure 5-amino-3-methylpyrazol (purity: 99%, yield: 39.6%).

Example 5

Into a 10-l separable flask were charged 186.3 g (1.80 moles) of cuprous chloride, 15.7 g (0.25 mole) of copper powder and 2,400 g of water. Thereto were simultaneously poured, with stirring at 65° C., 97.2 g (3.60 moles) of hydrocyanic acid and 580.7 g (1.57 moles) of 20% calcium hydroxide slurry to bring the pH of the resulting reaction mass to 3.5. Then the pH-adjusted reaction mass was brought up to 80° C. A liquid mixture of 1,344 g (12.00 moles) of 2,3-dichloropropene and 388.8 g (14.40 moles) of hydrocyanic acid was added thereto by drops at 80° C. over a period of 4.5 hours. During the period, 1,948.7 g (5.26 moles) of 20% calcium hydroxide slurry was added by drops to keep the pH of the reaction mass in the range of 3.3–3.9. The pH-controlled reaction mass was kept at the same temperature for additional 2 hours. During the period, 353.0 g (0.95 mole) of 20% calcium hydroxide slurry was added thereto by drops to keep the pH of the reaction mass in the range of 3.3–3.9.

After completion of the reaction, the reaction mass was cooled to room temperature. The cooled reaction mass was filtered and separated into layers to obtain 1,108.4 g of a light brown oil of crude 2,3-butadienenitrile containing 985.6 g (9.71 moles, yield: 80.9% based on 2,3-dichloropropene) of 3-chloro-3-butenonitrile and 19.2 g (0.30 mole, yield: 2.5% based on 2,3-dichloropropene) of 2,3-butadienenitrile.

Then, 34.24 g of the light brown oil of crude 2,3-butadienenitrile and 120 g of water were placed in a 500-ml flask and warmed to 30° C. A 28% aqueous sodium hydroxide solution was added to the mixture of crude 2,3-butadienenitrile and water by drops in the flask over a period of 8 hours while keeping the pH of the mixture at 9.4–10.0. After completion of the dropwise addition, the resulting mixture was allowed to stand and then separated into layers to obtain 20.15 g of a light brown oil. Then the aqueous layer was extracted with 120 g of dichloromethane. The extract was combined with the oil layer and distilled to obtain 19.95 g of a fraction containing 17.23 g (0.265 mole) of 2,3-butadienenitrile. The yield of 2,3-butadienenitrile was 72.1%.

Then 19.95 g of the fraction was added by drops over a period of 50 minutes to a liquid mixture of 25.14 g (0.30 mole) of 60% hydrazine hydrate and 100 ml of methanol while keeping the mixture at 5° C. or below. Then the resulting reaction mass was kept at the same temperature for 30 minutes. Thereafter, it was kept at 65° C. for 5 hours, 10.94 g (0.03 mole) of a 10% aqueous hydrochloric acid solution was added thereto, and the mass was kept at the temperature for additional 2 hours.

After completion of the reaction, the reaction mass was stripped of methanol and extracted with ethyl acetate. The extract was concentrated by distilling off ethyl acetate to obtain 28.79 g of crude 5-amino-3-methylpyrazole (purity: 86.0%, yield: 69.6% based on 2,3-dichloropropene). The crude product was purified by column chromatography to obtain 19.81 g of pure 5-amino-3-methylpyrazole (purity: 99%, yield: 67.1%).

Example 6

In a 50-ml autoclave were placed 0.015 g (0.15 mmole) of cuprous chloride, 0.165 g (1.65 mmoles) of calcium carbonate and 0.4 g of water. Then, the resulting mixture was cooled down to 4° C. 0.01 Gram (0.37 mmole) of hydrocyanic acid was added to the cooled mixture. The resulting reaction solution was brought up to 65° C., then kept at the same temperature for 15 minutes and cooled to 4° C. Then, 0.333 g (3 mmoles) of 2,3-dichloropropene and 0.125 g (4.63 mmoles) of hydrocyanic acid were fed into the autoclave. The resulting reaction mixture was brought up to 100° C. and kept at the same temperature with stirring for 10 hours. The pH of the reaction mixture was changed from 5.3 to 3.2 during the reaction.

After completion of the reaction, the reaction mass was cooled to 25° C. The cooled reaction mass was diluted with 20 ml of methylene chloride and dried over anhydrous magnesium sulfate. The magnesium sulfate was filtered off from the dried reaction mass. The filtrate and washings were combined, and the solvent was distilled off therefrom to obtain 0,308 g (2.97 mmoles) of 3-cloro-3-butenonitrile in the form of yellow oil (purity: 98%, yield: 99%).

The yellow oil thus obtained was dissolved in 10 ml of methanol. 0,571 Gram (6.84 mmoles) of 60% hydrazine was added to the oil. The resulting mixture was heated at 60° C. for 2 hours. After completion of the reaction, the reaction mixture was stripped of methanol, then treated with ethyl acetate to extract 5-amino-3-methylpyrazole, which was further purified by silica gel column chromatography to obtain 0.277 g (2.82 mmoles, purity: 99%, yield: 94% based on 2,3-dichloropropene) of 5-amino-3-methylpyrazole.

Example 7

Into 55.1 g of 60% hydrazine hydrate was added by drops at 70°-80° C. 26.7 g of a mixture of 1.9 g (0.03 mole) of 2,3-butadienenitrile and 24.6 g (0.24 mole) of 3-chloro-3-butenonitrile. The resulting mixture was kept at 80° C. for 1 hour and then cooled to room temperature to obtain 77.2 g of a pale yellow solution containing 25.5 g (0.26 mole) of 5-amino-3-methylpyrazole. (The yield of 5-amino-3-methylpyrazole was 97.1%).

To a 74.7 g portion (containing 24.7 g, 0.25 mole, as the pure compound, of 5-amino-3-methylpyrazole) of the 5-amino-3-methylpyrazole solution obtained above was added 43.4 g of concentrated hydrochloric acid. Then, with ice-cooling, 76.6 g of sulfuryl chloride was added thereto by drops at 25°-30° C. After the dropwise addition, the resulting mixture was allowed to react at 15°-20° C. for 3 hours, whereby 194.8 g of a reaction solution containing 5-amino-4-chloro-3-methylpyrazole hydrochloride was obtained. The reaction yield of 5-amino-4-chloro-3-methylpyrazole was 92.9%. Then 231 g of a 28% aqueous sodium hydroxide solution was added to the reaction solution containing 5-amino-4-chloro-3-methylpyrazole hydrochloride until the pH of the resulting solution became 7.

After neutralization, the neutralized reaction solution was extracted 4 times with 120 g of methyl t-butyl ether and organic layers were separated. Then, 26.1 g of concentrated hydrochloric acid was added by drops to the thus separated methyl t-butyl ether solution at 5°-10° C. The hydrochloric acid-added solution was kept at 5°-10° C. for 1 hour. The crystals precipitated from the thus treated solution were collected by filtration, washed with 50 g of acetone and dried to obtain 33.4 g of 5-amino-4-chloro-3-methylpyrazole hydrochloride. The yield of the hydrochloride was 77.8%. The purity of the hydrochloride determined by HPLC was 99.4%.

Example 8

Into 26.3 g of 60% hydrazine hydrate was added by drops at 70°-80° C. 26.7 g of a mixture of 3-chloro-3-butenonitrile and 2,3-butadienenitrile having the same composition as in Example 3. Then 37.6 g of a 28% aqueous sodium hydroxide solution was added thereto at 70°-80° C. The sodium-hydroxide added mixture was kept at 80° C. for 3 hours and then cooled to room temperature, whereby 92.4 g of a pale yellow solution containing 25.3 g (0.26 mole) of 5-amino-3-methylpyrazole was obtained (yield of 5-amino-3-methylpyrazole: 96.4%). To a 91.7 g portion of the 5-amino-3-methylpyrazole solution obtained above was added 43.4 g of concentrated hydrochloric acid. Then, with ice-cooling, 69.7 g (0.52 mole) of sulfuryl chloride was added to the hydrochloric acid-added mixture by drops at 25°-30° C. After the addition of sulfuryl chloride, the resulting mixture was allowed to react for 3 hours to give 204.5 g of a reaction solution containing 5-amino-4-chloro-3-methylpyrazole hydrochloride.

The reaction yield of 5-amino-4-chloro-3-methylpyrazole was 84.5%. To the reaction solution containing 5-amino-4-chloro-3-methylpyrazole hydrochloride was added 231.8 g of a 28% aqueous sodium hydroxide solution until the pH of the resulting solution became 7. After neutralization, the neutralized reaction solution was extracted 4 times with 120 g of t-butyl methyl ether and organic layers were separated. Then 26.1 g of concentrated hydrochloric acid was added by drops to the thus separated ethyl acetate solution at 5°-10° C. The hydrochloric acid-added solution was kept at 5°-10° C. for 1 hour. The crystals precipitated from the thus treated solution were collected by filtration, washed with 50 g of acetone, and dried to obtain 30.6 g of 5-amino-4-chloro-3-methylpyrazole hydrochloride. The yield of the hydrochloride based on the total of 3-chloro-3-butenonitrile and 2,3-butadienenitrile was 67%. The purity of the 5-amino-4-chloro-3-methylpyrazole hydrochloride determined by HPLC was 98%.

INDUSTRIAL APPLICABILITY

According to the process of the present invention, 5-amino-3-methylpyrazole can be synthesized by using 2,3-dichloropropene and hydrocyanic acid as starting materials without using such agents with the danger of spontaneous ignition as alkali metals and their hydrides.

Further, 5-amino-3-methylpyrazole can be subjected, without being isolated, to chlorination to obtain 5-amino-4-chloro-3-methylpyrazole hydrochloride, which is useful as an intermediate for medicines, agricultural chemicals and photographic chemicals.

We claim:

1. A process for producing 5-amino-3-methylpyrazole which comprises the steps of:
   (a) reacting 2,3-dichloropropene with hydrocyanic acid in the presence of water and a cuprous salt at a pH of from 3 to 8 to obtain a reaction intermediate comprising at least one compound selected from the group consisting of 3-chloro-3-butenonitrile and 2,3-butadienenitrile, and
   (b) reacting the reaction intermediate with hydrazine.

2. The process of claim 1, wherein the reaction of 2,3-dichloropropene with hydrocyanic acid is conducted at a pH of from 3 inclusive to 6 exclusive.

3. The process of claim 1, wherein the reaction of 2,3-dichloropropene with hydrocyanic acid is conducted at a pH of from 3 to 5.

4. The process of claim 1, wherein the reaction of 2,3-dichloropropene with hydrocyanic acid is conducted at a pH of from 6 to 8.

5. A process for producing 5-amino-3-methylpyrazole which comprises the steps of:
   (a) reacting 2,3-dichloropropene with hydrocyanic acid in the presence of water and a cuprous salt at a pH of from 3 to 8 to obtain a reaction mixture containing 3-chloro-3-butenonitrile, (b) reacting a base with the reaction mixture to obtain 2,3-butadienenitrile, and (c) reacting 2,3-butadienenitrile with hydrazine.

6. The process of claim 5, wherein the reaction of 2,3-dichloropropene with hydrocyanic acid is conducted at a pH of from 3 inclusive to 6 exclusive.

7. The process of claim 5, wherein the reaction of 2,3-dichloropropene with hydrocyanic acid is conducted at a pH of from 3 to 5.

8. The process of claim 1, wherein the reaction of 2,3-dichloropropene with hydrocyanic acid is conducted in the presence of calcium hydroxide or calcium carbonate.

* * * * *